(12) United States Patent  
Robbins et al.

(10) Patent No.: US 8,512,367 B2  
(45) Date of Patent: Aug. 20, 2013

(54) BLOOD SAMPLING DEVICE WITH DUAL-LINK DRIVE MECHANISM

(75) Inventors: Avi M. Robbins, Augusta, GA (US); Gil Kan, Atlanta, GA (US)

(73) Assignee: Facet Technologies, LLC, Kennesaw, GA (US)

( * ) Notice: Subject to any disclaimer, the term of this patent is extended or adjusted under 35 U.S.C. 154(b) by 478 days.

(21) Appl. No.: 12/712,761

(22) Filed: Feb. 25, 2010

(65) Prior Publication Data

US 2011/0144537 A1 Jun. 16, 2011

Related U.S. Application Data

(60) Provisional application No. 61/287,085, filed on Dec. 16, 2009.

(51) Int. Cl.
*A61B 5/00* (2006.01)

(52) U.S. Cl.
USPC .................................................. 606/182

(58) Field of Classification Search
USPC ................................. 600/583; 606/181–183
See application file for complete search history.

(56) References Cited

U.S. PATENT DOCUMENTS

| | | | |
|---|---|---|---|
| 3,760,809 A | 9/1973 | Campbell, Jr. | |
| D228,815 S | 10/1973 | Campbell | |
| D245,040 S | 7/1977 | Thomas | |
| 4,064,871 A | 12/1977 | Reno | |
| D248,046 S | 5/1978 | Tada | |
| 4,539,988 A | 9/1985 | Shirley et al. | |
| 4,628,929 A | 12/1986 | Intengan et al. | |
| 4,643,189 A | 2/1987 | Mintz | |
| 4,715,374 A | 12/1987 | Maggio | |
| 4,735,203 A | 4/1988 | Ryder et al. | |
| D297,978 S | 10/1988 | White | |
| 4,892,097 A | 1/1990 | Ranalletta et al. | |
| 4,924,879 A | 5/1990 | O'Brien | |
| 5,035,704 A | 7/1991 | Lambert et al. | |
| 5,133,730 A | 7/1992 | Biro et al. | |
| 5,196,025 A | 3/1993 | Ranalletta et al. | |
| 5,212,879 A | 5/1993 | Biro et al. | |
| 5,314,441 A * | 5/1994 | Cusack et al. | 606/182 |
| 5,395,388 A | 3/1995 | Schraga | |
| 5,397,334 A | 3/1995 | Schenk et al. | |
| 5,476,474 A | 12/1995 | Davis et al. | |
| 5,514,152 A | 5/1996 | Smith | |

(Continued)

FOREIGN PATENT DOCUMENTS

JP 2000245715 9/2000

*Primary Examiner* — Max Hindenburg
(74) *Attorney, Agent, or Firm* — Gardner Groff Greenwald & Villanueva, PC

(57) ABSTRACT

A housing and an internal mechanism including a blade, a dual-link drive mechanism, and a trigger. The blade is driven by the drive mechanism through a rotating and translating slicing motion that defines a sampling sequence, from a first retracted position to an extended position to a second retracted position. The dual-link drive mechanism includes a blade link arm coupled to the blade, a rotary drive link arm that drives the blade arm, a drive spring that drives the a rotary drive arm, and a cam-and-follower mechanism that guides the blade arm as it is driven by the rotary drive arm. The trigger is operable to release the dual-link drive mechanism to propel the blade through the sampling sequence. And a sterility cap protects the blade and prevents operation of the device prior to removal.

18 Claims, 8 Drawing Sheets

(56) References Cited

U.S. PATENT DOCUMENTS

| | | |
|---|---|---|
| 5,518,006 A | 5/1996 | Mawhirt et al. |
| 5,527,333 A | 6/1996 | Nikkels et al. |
| 5,527,334 A | 6/1996 | Kanner et al. |
| 5,545,174 A | 8/1996 | Schenk et al. |
| D374,719 S | 10/1996 | Py |
| 5,571,132 A | 11/1996 | Mawhirt et al. |
| 5,628,765 A | 5/1997 | Morita |
| 5,645,555 A | 7/1997 | Davis et al. |
| 5,772,677 A | 6/1998 | Mawhirt et al. |
| 5,776,157 A | 7/1998 | Thorne et al. |
| 5,782,852 A | 7/1998 | Foggia et al. |
| 5,797,940 A | 8/1998 | Mawhirt et al. |
| 5,951,582 A | 9/1999 | Thorne et al. |
| 6,010,519 A | 1/2000 | Mawhirt et al. |
| 6,042,595 A | 3/2000 | Morita |
| D422,697 S | 4/2000 | Bellhouse et al. |
| 6,221,089 B1 * | 4/2001 | Mawhirt ........................ 606/181 |
| D450,614 S | 11/2001 | Wilkinson |
| 6,409,740 B1 | 6/2002 | Kuhr et al. |
| 6,858,015 B2 * | 2/2005 | List .............................. 600/583 |
| 6,929,649 B2 | 8/2005 | Pugh |
| 7,144,404 B2 | 12/2006 | Whitson et al. |
| 7,160,313 B2 | 1/2007 | Galloway et al. |
| D557,807 S | 12/2007 | McCarty |
| 7,316,698 B1 | 1/2008 | Galloway et al. |
| D566,273 S | 4/2008 | Gutmann et al. |
| D581,533 S | 11/2008 | Ruf et al. |
| 7,452,365 B2 | 11/2008 | Galloway et al. |
| 7,510,564 B2 | 3/2009 | Mace |
| 7,691,117 B2 * | 4/2010 | Whitson et al. ................ 606/182 |
| 7,704,265 B2 * | 4/2010 | Schraga ........................ 606/182 |
| 2005/0131441 A1 | 6/2005 | Iio et al. |
| 2005/0154410 A1 | 7/2005 | Conway et al. |
| 2005/0256534 A1 | 11/2005 | Alden et al. |
| 2005/0283177 A1 | 12/2005 | Chen |
| 2006/0106411 A1 | 5/2006 | Schraga |
| 2006/0259057 A1 | 11/2006 | Kim et al. |
| 2006/0259060 A1 | 11/2006 | Whitson et al. |
| 2006/0264997 A1 | 11/2006 | Colonna et al. |
| 2007/0032813 A1 | 2/2007 | Flynn et al. |
| 2007/0095178 A1 | 5/2007 | Schraga |
| 2007/0225741 A1 | 9/2007 | Ikeda |
| 2008/0097502 A1 | 4/2008 | Winters-Hilt et al. |
| 2009/0054812 A1 | 2/2009 | Mace |
| 2009/0099586 A1 | 4/2009 | Koeppel et al. |

* cited by examiner

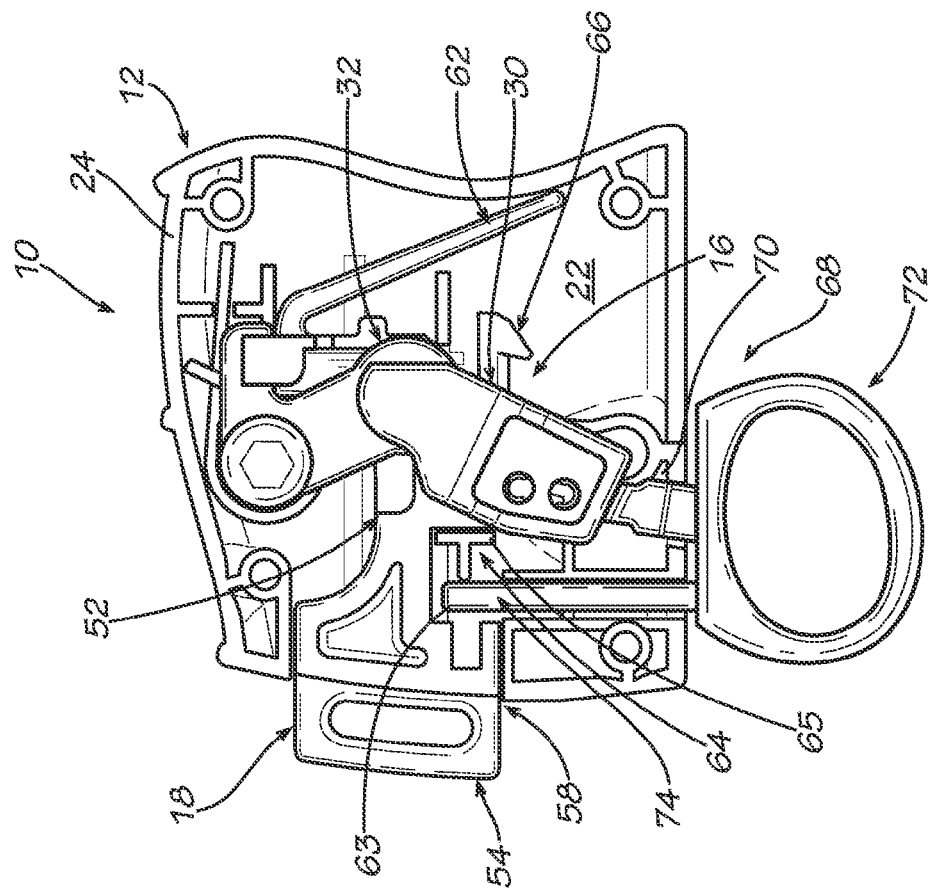
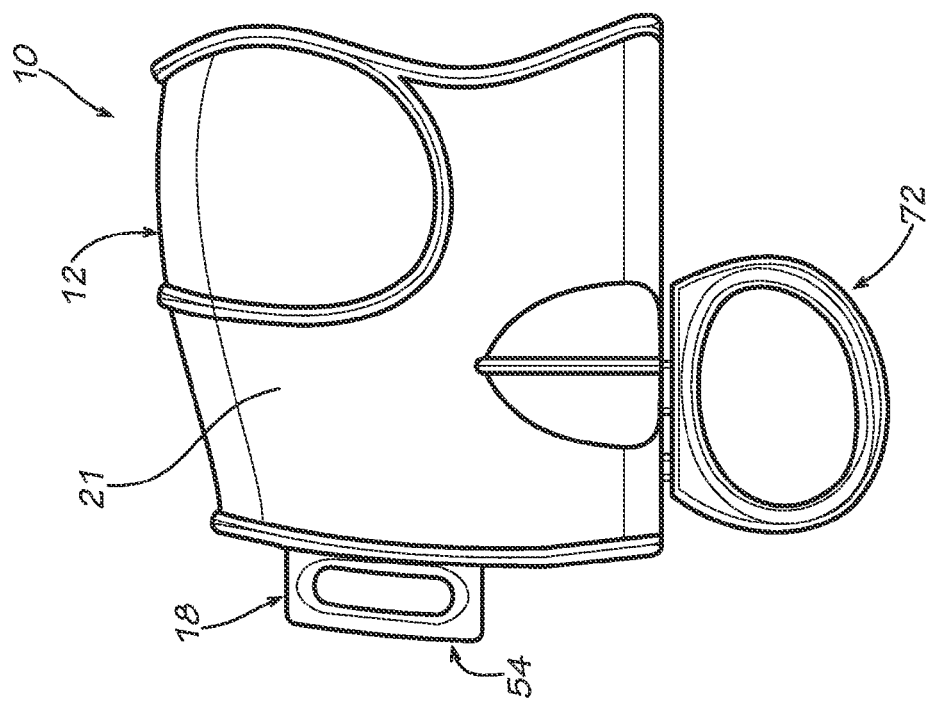
FIG. 2
FIG. 1

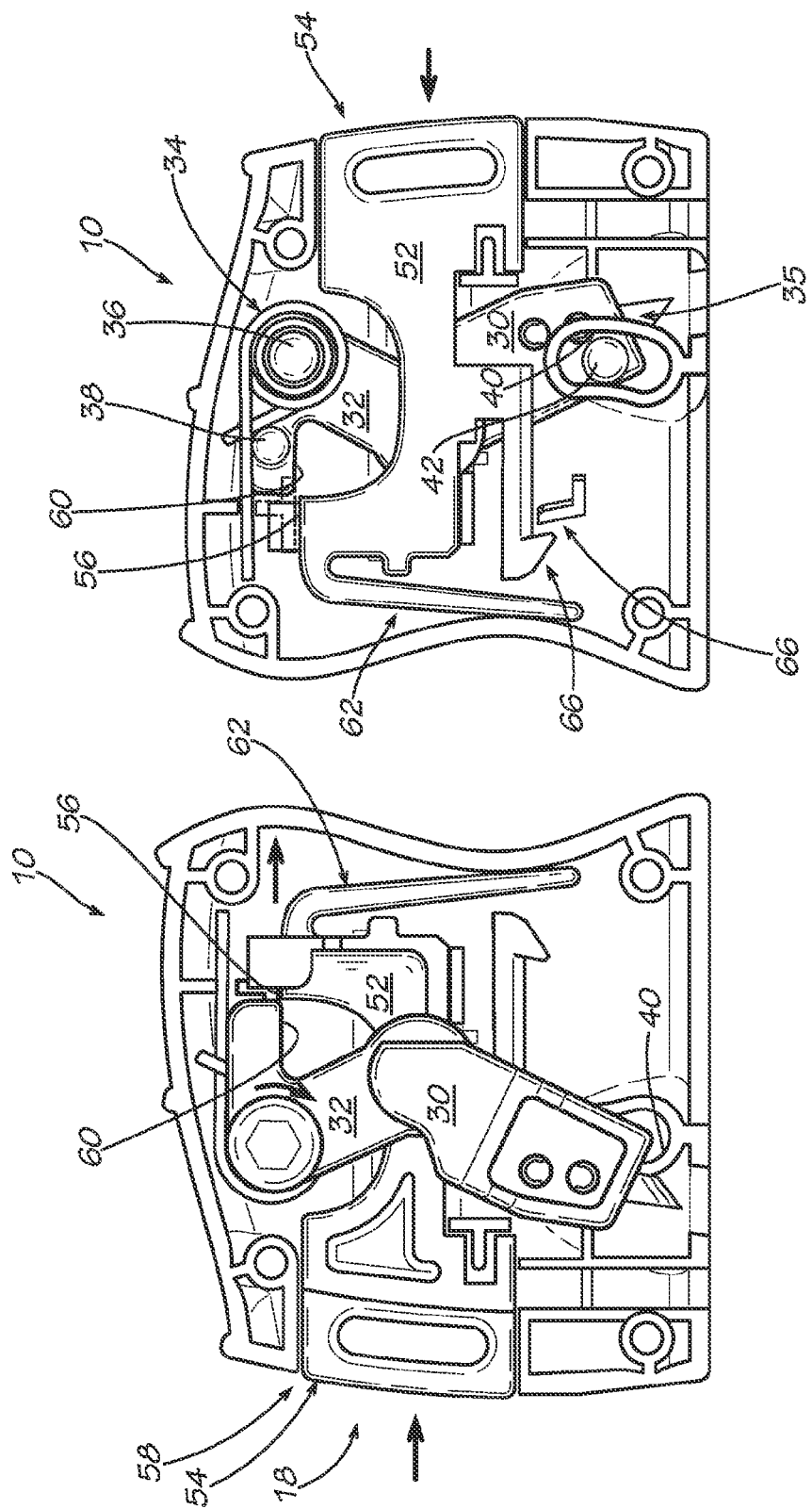

BLOOD SAMPLING DEVICE WITH DUAL-LINK DRIVE MECHANISM

CROSS-REFERENCE TO RELATED APPLICATION

This application claims the priority benefit of U.S. Provisional Patent Application Ser. No. 61/287,085, filed Dec. 16, 2009, which is hereby incorporated herein by reference.

TECHNICAL FIELD

The present invention relates generally to the field of medical devices and, more particularly, to medical devices for generating samples of blood from humans or other animals.

BACKGROUND

Medical fluid-sampling devices such as lancets and lancing devices are commonly used for penetrating the skin of a human or animal subject at a sampling site to obtain a sample of blood or other body fluid for medical testing. Such blood sampling is commonly done on neonates and adults for blood-typing, glucose-testing, etc. Known blood-sampling devices commonly include a housing containing a drive mechanism and a trigger/release mechanism for actuating the drive mechanism. A lancet is typically propelled by the drive mechanism from a retracted position shielded within the housing to an extended position where a sharp needle or blade tip of the lancet projects from the housing to penetrate the subject's skin at the lancing site. Common problems with conventional blood-sampling devices include vibrations that can cause increased pain, complicated designs that result in high manufacturing costs, etc.

Accordingly, needs exist for improvements to blood-sampling devices. It is to the provision of improved blood-sampling devices that the present invention is primarily directed.

SUMMARY

Generally described, the invention relates to a medical device for penetrating skin to generate a sample of fluid such as blood. The device includes a housing having a blade opening, a blade having a sharp tip that travels along a travel path, a dual-link drive mechanism that drives the blade along its travel path, and a trigger that actuates the drive mechanism to propel the blade tip along its travel path. The blade tip travels along its travel path from a retracted position shielded within the housing to an extended position extending through the blade opening to precisely penetrate the skin.

In one aspect, the dual-link drive mechanism can include a blade arm, a rotary drive arm, and a cam-and-follower guide mechanism. The blade arm and the drive arm are the two links, and no other drive link is needed to produce the precision blade-tip travel path. The blade arm is coupled to the blade. The rotary drive arm is pivotally coupled to and drives the blade arm. And the cam-and-follower mechanism guides the movement of the blade arm. The drive arm and the cam-and-follower mechanism together work to drive and guide the blade arm to propel the blade tip along its travel path in a rotational and translating motion. The cam-and-follower mechanism includes a cam surface and a cam follower that is guided by the cam surface so that rotary motion of the rotary drive arm is converted to the rotational and translating motion of the blade tip. As the drive arm rotationally drives the blade arm, the blade arm rotates about the cam follower as the cam follower is translationally guided along the cam surface, thereby converting the rotary motion of the rotary drive arm to the rotational and translating motion of the blade tip.

In a typical commercial embodiment, the cam surfaced is defined by a channel formed in the housing, and the cam follower is provided by a pin on the blade arm that slides within the channel. The cam follower is intermediately positioned on the blade arm between the blade and pivotal coupling to the drive arm.

In another aspect, the cam surface can be generally vertical (i.e., perpendicular to the skin) and curved so that the blade travel path is non-linear. For example, the curved cam surface can be arranged so that the blade travel path is generally triangular and has a slightly curved descent segment and a slightly curved ascent segment that is steeper than the descent segment. The descent segment occurs as the blade tip travels from the retracted position to the extended position, and the ascent segment occurs as the blade tip travels from the extended position to a second retracted position again shielded within the housing.

In addition, the drive mechanism can also include a drive spring that biases the rotary drive arm in a drive direction and a catch surface that is engaged by the trigger to retain the drive arm in a ready position. And the sampling device can also include a removable sterility cap with a shroud portion that fits over the blade tip when it's in the retracted position. The trigger can have a blocked surface and the sterility cap can have a blocking member that contacts the trigger blocked surface to prevent the trigger from being inadvertently actuated.

These and other aspects, features, and advantages of the invention will be understood with reference to the drawing figures and detailed description herein, and will be realized by means of the various elements and combinations particularly pointed out in the appended claims. It is to be understood that both the foregoing general description and the following brief description of the drawings and detailed description of the invention are exemplary and explanatory of example embodiments of the invention, and are not restrictive of the invention, as claimed.

BRIEF DESCRIPTION OF THE DRAWINGS

FIG. 1 is a right side view of a blood sampling device according to a first example embodiment of the present invention, shown in a first or initial state.

FIG. 2 shows the blood sampling device of FIG. 1 with the right sidewall of the housing removed to show the internal components.

FIG. 5 shows the blood sampling device of FIG. 2 in a third state, after the user presses the actuator to release the drive mechanism.

FIG. 6 is a left side view of the blood sampling device of FIG. 5 with the left side of the housing removed to show the internal components.

DETAILED DESCRIPTION OF EXAMPLE EMBODIMENTS

Figure 4:
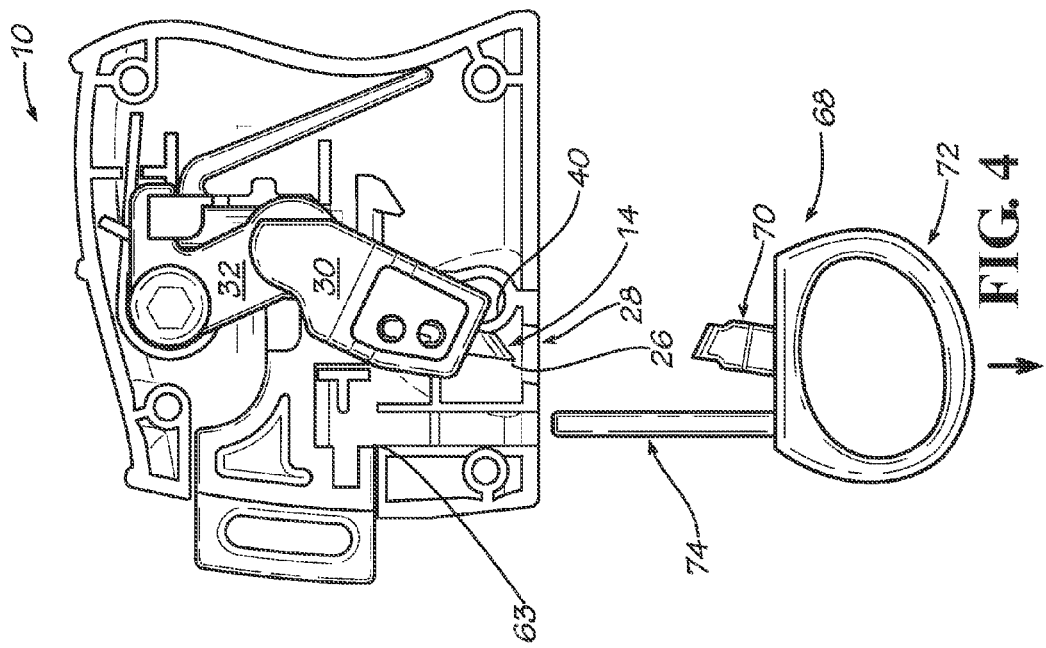
FIG. 4 shows the blood sampling device of FIG. 3 with the right side of the housing removed to show the internal components.

The present invention may be understood more readily by reference to the following detailed description taken in connection with the accompanying drawing figures, which form a part of this disclosure. It is to be understood that this invention is not limited to the specific devices, methods, conditions, or parameters described and/or shown herein, and that the terminology used herein is for the purpose of describing particular embodiments by way of example only and is not intended to be unnecessarily limiting of the claimed invention. Any and all patents and other publications identified in this specification are incorporated by reference as though fully set forth herein.

Also, as used in the specification including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

With reference now to the drawing figures, FIGS. 1-11 show a blood-sampling device 10 according to a first example embodiment of the invention. The depicted device 10 is useful for generating blood samples from neonates. The device 10 is designed primarily for neonates because in adults blood can be easily taken from the veins on the person's arm, and clinical studies have shown that heel-stick methods are better than regular puncture methods on the heels of infants for newborn screenings. In embodiments for neonatal use, the housing and internal components typically are relatively smaller. In alternative embodiments that can be used for adults, the housing and internal components typically are relatively larger. The device can be provided in disposable, single-use embodiments, as is depicted, or in multi-use embodiments in which the blades are sequentially replaced or advanced (e.g., within a blade cartridge).

Referring primarily to FIGS. 2, 4, 6, and 8, the device 10 includes a housing 12 and an internal mechanism including a blade 14, a dual-link drive mechanism 16 for propelling the blade through a sampling sequence, and a trigger mechanism 18 for actuating the drive mechanism. The housing 12 of the depicted embodiment includes a right sidewall 20, an opposing left sidewall 22, and a peripheral endwall 24 extending between them. Alternatively, the housing can be configured in other ways well-known in the art.

The blade 14 has a sharp edge with a tip 26. The blade tip 26 moves through the sampling sequence from a first retracted position, to an extended position, and to a second retracted position. In the first retracted position (see FIGS. 1-6) and the second retracted position (see FIGS. 9-10), the blade tip 26 is shielded within the housing 12. In the extended position (see FIGS. 7-8), the blade tip 26 projects out of the housing 12 through a blade opening 28 to penetrate the skin at a desired sampling site.

The dual-link drive mechanism 16 includes a blade link arm 30, a rotary drive link arm 32, a drive spring 34, and a cam-and-follower guide mechanism 35. The blade 14 is fixedly attached to the blade arm 30. For example, the blade 14 can be fixedly attached to the blade arm 30 at its distal end by conventional fasteners such as pins or screws or by overmolding. Alternatively, the blade 14 and the blade arm 30 can be integrally formed as a single piece, or in multi-use embodiments the blade 14 can be replaceable on the blade arm 30. The blade arm 30 is pivotally coupled to and driven by the rotary drive arm 32. For example, a proximal end of the blade arm 30 can be pivotally coupled to a distal end of the rotary drive arm 32 by a conventional pivotal fastener such as a non-binding pin received in an aperture or recess. Alternatively, the blade arm 30 can be replaceable on the rotary drive arm 32 in multi-use embodiments. The rotary drive arm 32 is rotationally mounted to the housing 12. For example, the rotary drive arm 32 can be rotationally mounted to the housing 12 by a non-binding pin 36 that extends laterally from the drive arm and is received in a recess in the internal surface of the right or left sidewall 20 and 22 of the housing. In an alternative embodiment, the rotary drive arm can be rotationally mounted to the housing by two non-binding pins that extend laterally from opposite sides of the drive arm and are received in two recesses in the internal surfaces of the right and left sidewalls of the housing. The drive spring 34 biases the rotary drive arm 32 in a rotational drive direction to drive the blade arm 30 through the sampling sequence. For example, the drive spring 34 can be provided by a torsion spring mounted about the mounting pin(s) 36 for the rotary drive arm 32, with one end engaging and biasing a drive pin or other surface 38 on the rotary drive arm in the rotational drive direction and with the other end engaging and biasing against the housing 12. Alternatively, the drive spring 34 can be provided by a leaf spring, a compression coil spring, a tension coil spring, an elastic member, or another conventional spring element selected to drive the rotary drive arm in the rotational drive direction.

The cam-and-follower guide mechanism 35 of the dual-link drive mechanism 16 includes a cam surface 40 and a cam follower 42. The cam follower 42 is guided by the cam surface 40 so that the rotary motion of the rotary drive arm 32 is converted to a combined rotary and translating "slicing" motion of the blade 14. For example, the cam surface 40 can be defined by a sidewall of a channel 44 formed (e.g., by a recess in the housing or by walls extending from the housing) into the left sidewall 22 of the housing 12. (Note that in FIGS. 6, 8, and 10, the left sidewall 22 is not shown but the cam surface 40 that extends inwardly from it is shown.) Alternatively, the cam surface 40 can be defined by a sidewall projecting inwardly from the housing 12. And the cam follower 42 can be provided by a pin (e.g., a finger, rod, arm, tab, or other projecting member) that extends from the blade arm 30 and is slidingly received in the channel 44. The cam follower 42 is intermediately positioned on the blade arm 30 between the blade 14 (e.g., at the blade arm's distal end) and the pivotal coupling to the rotary drive arm 32 (e.g., at the blade arm's proximal end). In this way, as the drive arm 32 rotationally drives the proximal end of the blade arm 30, the blade arm rotates about the cam follower 42 as the cam follower is translationally guided along the cam surface 40, resulting in the rotational/translational slicing motion by the blade 14. Alternatively, the positions of the cam surface 40 and the cam follower 42 can be switched, with the cam surface formed on the blade arm 30 and the cam follower formed on the housing 12.

Figure 11:
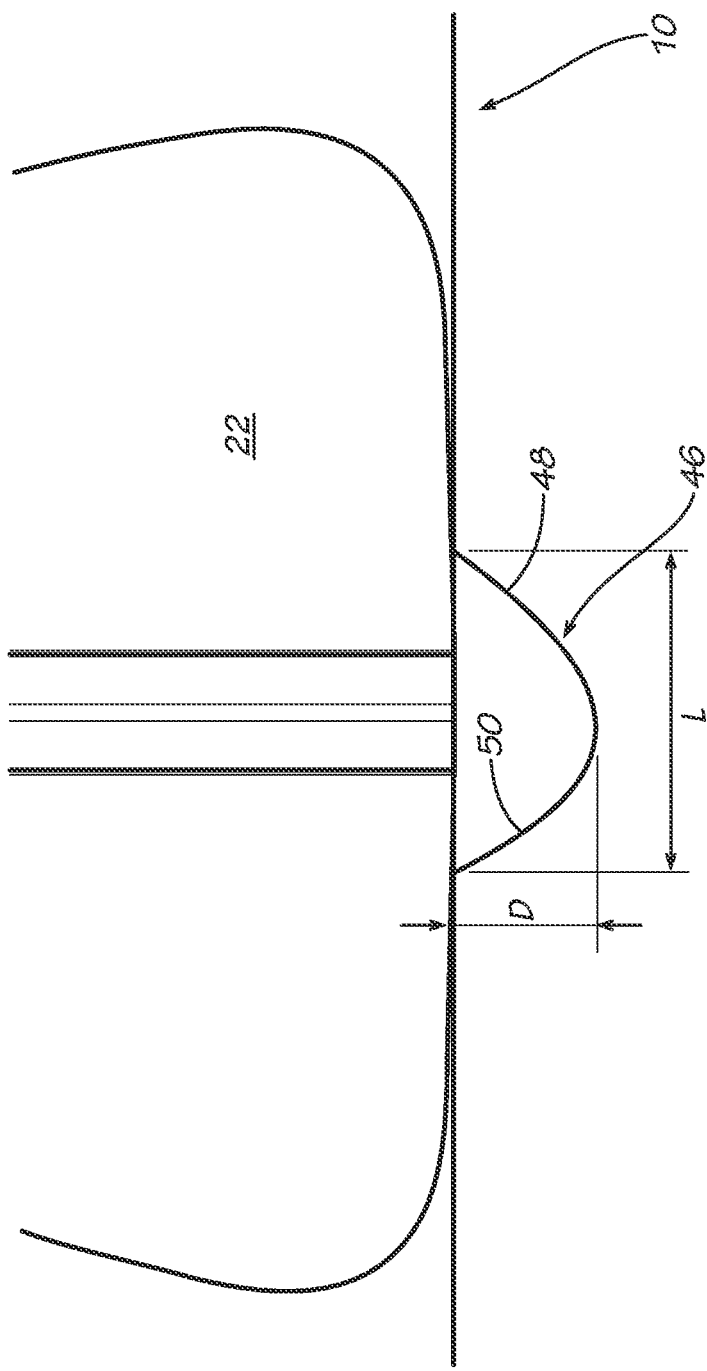
FIG. 11 is a left side detail view of a portion of the blood sampling device of FIG. 1 showing the travel path of the blade tip as it moves through the blood-sampling sequence shown in FIGS. 1-10.

Referring additionally to FIG. 11, the cam surface 40 can be generally vertical (i.e., generally perpendicular to the skin at the sampling site) but non-linear and slightly curved so that the descent path segment 48 of the travel path 46 of the blade tip 26 during the sampling sequence is less steep/sloped than the ascent path segment 50. This generally produces a less painful incision, allowing the blade 16 to more gently incise the skin in its more gradual descent and then withdrawing the blade from the skin more quickly to minimize the length of the incision. In addition, the cam surface 40 produces a blade-tip travel path 46 that is generally triangular, that is, approximating a "V" shape but rounded where the blade tip 26 is in or near the extended position, with slightly curved sides (i.e., the descent and ascent segments), and non-symmetrical with one side longer and less-sloped than the other. In a typical commercial embodiment for use on full-term neonates, the travel path 46 of the blade tip 26 has a length L of about 2.5 inches and a depth D of about 1.0 inches. In typical commercial embodiments for use on preemies and micro-preemies, the travel path 46 of the blade tip 26 has a shorter length L and depth D. Alternatively, the cam surface can be linear to produce identical descent and ascent travel path segments and/or can be configured differently so that the travel path has a non-triangular shape and/or other dimensions (e.g., other lengths and depths).

The trigger mechanism 18 is operable to actuate the dual-link drive mechanism 16 to propel the blade 14 through the sampling sequence. The trigger 18 includes a main body 52 defining an external actuator portion 54 and a catch surface 56. The actuator 54 extends through an actuator opening 58 in the housing 12 so that it can be moved by the user from a ready position to an actuated position. The catch surface 56 engages a cooperating catch 60 defined by the rotary drive arm 32 to retain the rotary drive arm in a ready/charged position when the actuator 54 is in the ready position. And the trigger catch surface 56 disengages from the drive catch 60 when the actuator 54 is moved to the actuated position, thereby releasing the rotary drive arm 32 to proceed with the sampling sequence. In addition, the trigger mechanism 18 includes a trigger spring 62 that biases the actuator 54 toward the ready position. In the depicted embodiment, for example, the actuator 54 is a button that is pushed by the user from the ready to actuated positions and the trigger spring 62 is provided by a leaf spring that is cantilevered from the trigger body 52 and biases against an internal surface of the housing 12. In other embodiments, the actuator is pulled or rotated from the ready to actuated positions and/or the trigger spring is provided by a tension or compression coil spring or another resilient or elastic member. Furthermore, the depicted embodiment includes mechanical stops 63, 64, 65 on the trigger body 52 and the housing 12 for retaining the trigger 18 from being pulled out of the housing 12 when in the ready position and for limiting the trigger from being moved past the actuated position. And mechanical stops 66 are also provided on the trigger body 52 and the housing 12 for retaining the trigger 18 in the actuated position after use. (Note that in FIGS. 6, 8, and 10, the left sidewall 22 is not shown but the other mechanical stop 66, which extends inwardly from it, is shown.)

In addition, the blood-sampling device 10 can be provided with a sterility cap that protects the blade 14 prior to use. In the depicted embodiment, for example, the blood-sampling device 10 includes a sterility cap 68 having a shroud portion 70 and an external actuator portion 72. The sterility cap shroud 70 is fitted onto and covers the blade tip 26, and extends through the blade opening 28 of the housing 12. The actuator portion 72 is graspable by the user to pull the shroud 70 off the blade 14. In the depicted embodiment, for example, the actuator portion 72 is in the form of a finger loop. In addition, the sterility cap 68 can include a blocking member 74 that contacts a blocked surface (e.g., stop surface 63) of the trigger 18 when the sterility cap 68 is mounted on the blade 14, with the contacting interference preventing the trigger from being fired. When the sterility cap 68 is removed from the blade 14 by the user, the blocking member 74 is removed from interference with the blocked surface 76 of the trigger 18, thereby permitting the trigger to be fired.

The blood-sampling device 10 can be manufactured using materials and techniques that are well-known in the art. The housing 12, the trigger 18, the blade arm 30, the rotary drive arm 32, and the cam-and-follower mechanism 35 can be made of a hard plastic material using conventional fabrication techniques such as molding. The blade 14 and the drive spring 34 can be made of a metal (e.g., steel) or a hard plastic. To assemble the device 10, the rotary drive arm 32 and the drive spring 34 can be mounted in place, the rotary drive arm can be rotated against the force of the drive spring to the ready position, and then the trigger 18 can be mounted in the ready position. The rotary drive arm 32 can be so rotated for example by an ALLEN wrench that fits into a mating recess in the rotary drive arm.

Having described structural details of the blood-sampling device 10, its operation and use will now be described. FIGS. 1 and 2 show the device 10 in the first or initial state. In this state, the sterility cap 68 is in the mounted position with the shroud portion 70 on the blade 14 to protect it from contamination, the blocking portion 74 interfering with the trigger 18 so it cannot be moved to the actuated position, and the trigger spring 62 biasing the trigger 18 toward the ready position. Because the blocking portion 74 interferes with the trigger 18, the device 10 cannot be accidentally fired before its intended use by a user or during shipment.

Figure 3:
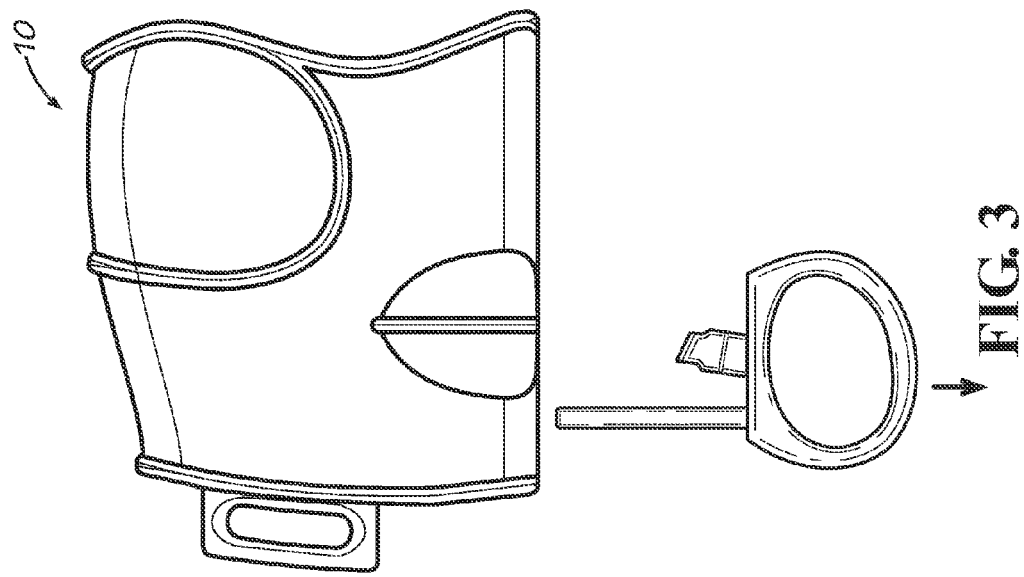
FIG. 3 shows the blood sampling device of FIG. 1 in a second state, after detachment of the sterility cap.

The sampling sequence begins by the user removing the sterility cap 68 from the blade 14. FIGS. 3 and 4 show the device 10 in the second state, after detachment of the sterility cap, with the trigger 18 in its ready position and the blade 14 in its retracted position. The drive spring 34 is in its charged position biasing the drive arm 32 in the rotational drive direction and the cam follower 42 is at the top of the cam surface 40.

After the sterility cap 68 has been removed, the user depresses the actuator 54 of the trigger 18. This causes the trigger 18 to move from the ready position to the actuated position. FIGS. 5 and 6 show the device 10 in the third state, with the trigger 18 in actuated position. When the trigger 18 is moved to the actuated position, the trigger catch 56 disengages from the drive catch 60, releasing the dual-link drive mechanism 16. The drive spring 34 then begins to rotationally drive the rotary drive arm 32 in the direction indicated by the directional arrow.

Figure 8:
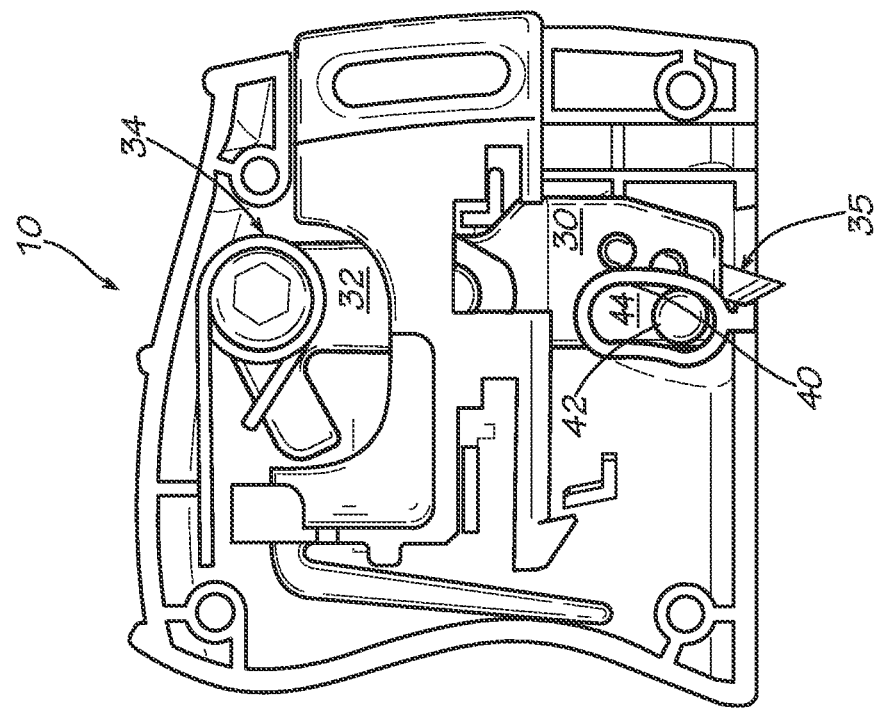
FIG. 8 is a left side view of the blood sampling device of FIG. 7 with the left side of the housing removed to show the internal components.
Figure 7:
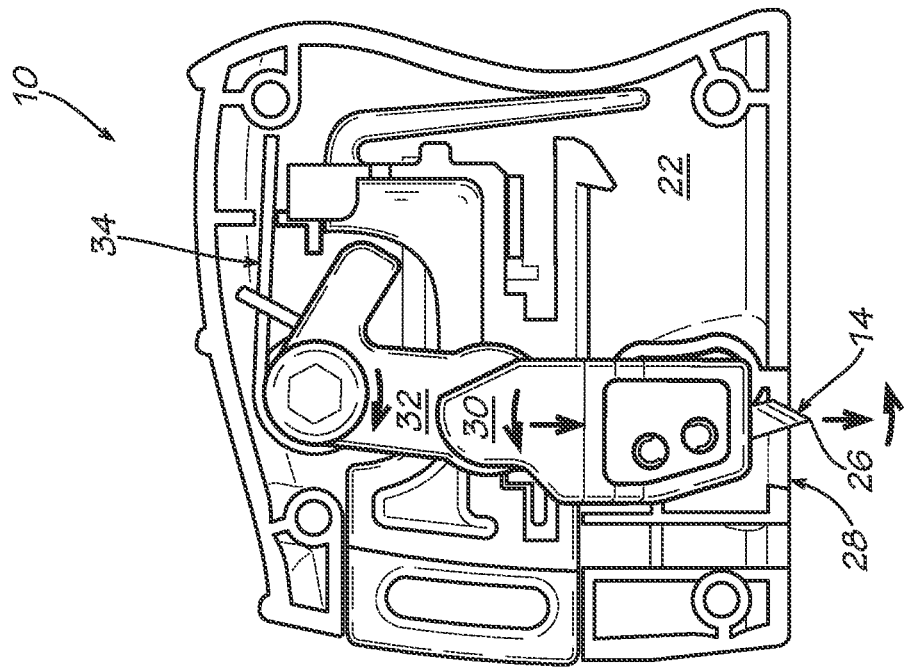
FIG. 7 shows the blood sampling device of FIG. 2 in a fourth state, as the blade is generating the incision at the sampling site.

FIGS. 7 and 8 show the device 10 in the fourth state, with the blade 14 in the extended position generating the incision at the sampling site. As the drive spring 34 rotates the drive arm 32 in the drive direction, the drive arm in turn rotationally drives the blade arm 30 about the cam follower 42, as indicated by the rotary directional arrow. At the same time, the cam follower 42 on the blade arm 30 slides along the cam surface 40 of the housing 12, with the cam and follower guiding the blade arm in a translating motion, as indicated by the linear directional arrow. Thus, the blade 14 is driven by the drive mechanism 16 and guided by the cam-and-follower mechanism 35 in a combined rotating and translation motion that results in a slicing action. In the extended position depicted, the cam follower 42 is at the bottom of the cam surface 40.

Figure 9:
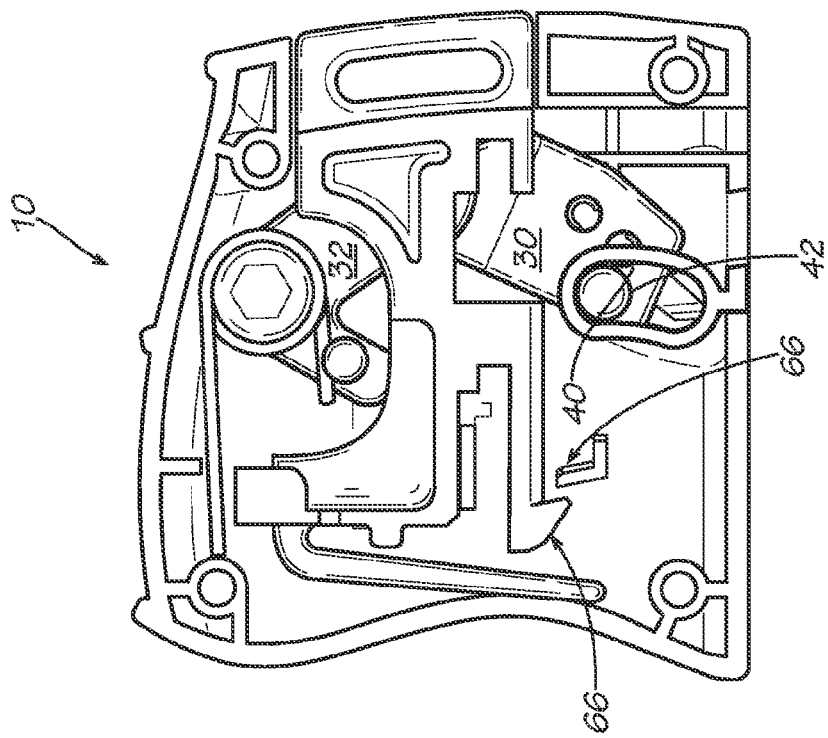
FIG. 9 shows the blood sampling device of FIG. 2 in a fifth state, at the end of the sequence of operation.
Figure 10:
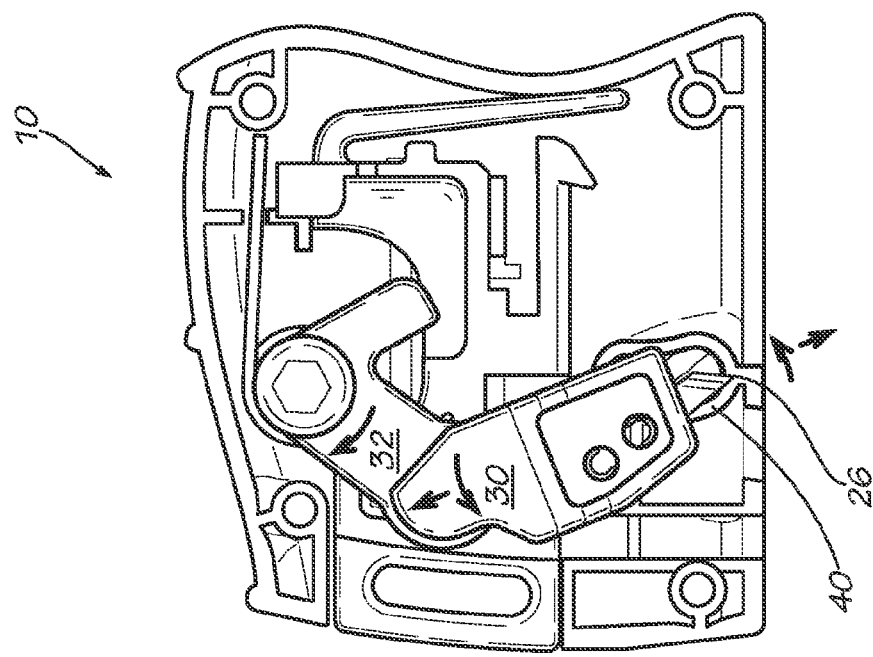
FIG. 10 is a left side view of the blood sampling device of FIG. 9 with the left side of the housing removed to show the internal components.

FIGS. 9 and 10 show the device 10 in a fifth state, at the end of the sequence of operation. The drive arm 32 and the cam-and-follower mechanism 35 have continued driving and guiding the blade arm 30, which is now in the second retracted position. In this position, the blade 14 is fully retracted to within the housing 12 (and held there by the biasing force of the drive spring 34) and the trigger 18 is held in the actuated position by the mechanical stops 66. With the trigger 18 held in the actuated position by the mechanical stops 66, it is clear that the device 10 has already been used, and the device cannot be re-used. The cam follower 42 is now back at the top of the cam surface 40. The sampling sequence is now completed, with the sharp tip 26 of the blade 14 having completed its travel path 46, which is shown in FIG. 11.

To use the blood-sampling device 10, a sampling site is selected and the blade opening 28 of the housing 12 is placed against the skin at the selected site. Then the actuator button 54 is depressed to start the sampling sequence. At the conclusion of the sampling sequence, the device 10 is removed from the sampling site and the sample generated by the sampling sequence is collected and processed. The device 10 is then discarded (in disposable/single-use embodiments) or a fresh lancet is inserted or advanced for use (in multi-lancet/multi-use embodiments).

Figure 12:
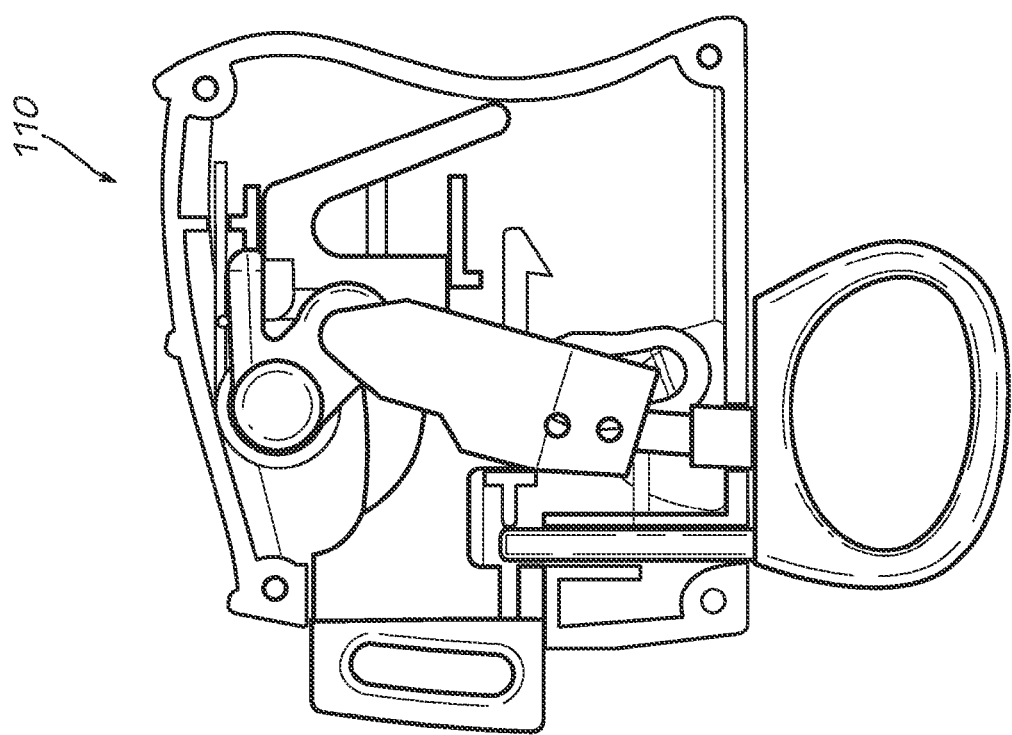
FIG. 12 is a right side view of a blood sampling device according to a second example embodiment of the present invention, shown in a first or initial state with the right sidewall of the housing removed to show the internal components.
Figure 13:
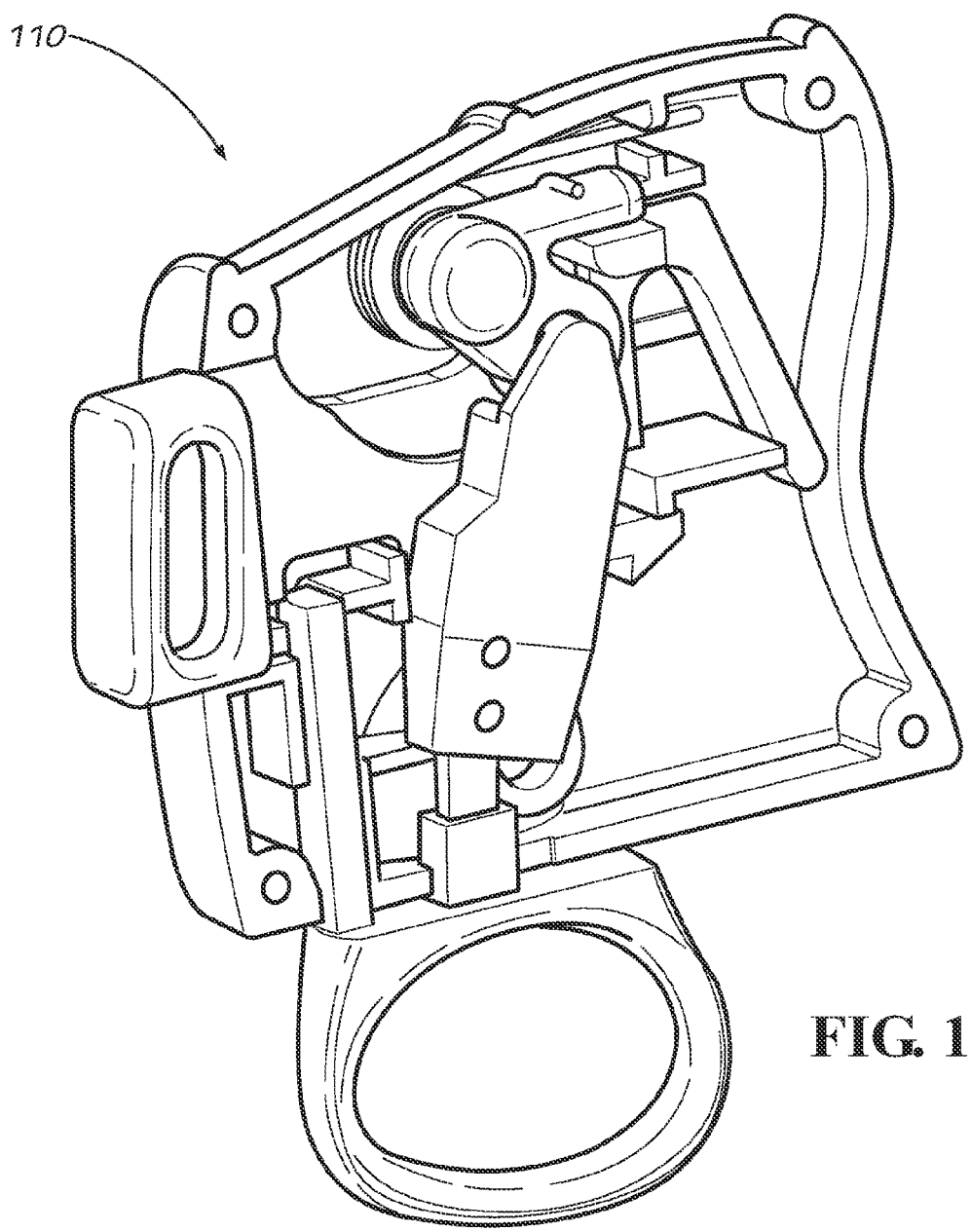
FIG. 13 is a perspective view of the blood sampling device of FIG. 12.

FIGS. 12 and 13 show a blood sampling device 110 according to a second example embodiment of the present invention. The design, manufacture, operation, and use of the device 110 of this embodiment are substantially the same as those of the above-described embodiment, expect for minor differences such as some dimensions.

In alternative embodiments, the dual-link drive mechanism is adapted for inclusion in re-usable blood-sampling devices. In one such embodiment, the blade is replaceable on the drive arm, for example, by a snap-fit coupling between the drive arm and a blade body mounted to the blade, and the sterility cap screws onto and off of the blade body. In this way, the sterility cap can be removed by unscrewing it from the blade body, and then the sampling device can be used. Then the sterility cap can be screwed back onto the blade body, the sterility cap then can be pulled to remove it and the blade body (and the blade) from the drive arm, and a replacement sterility cap/blade body/blade assembly then can be snapped onto the drive arm for subsequent use.

While the invention has been described with reference to preferred and example embodiments, it will be understood by those skilled in the art that a variety of modifications, additions and deletions are within the scope of the invention, as defined by the following claims.

What is claimed is:

1. A fluid-sampling device for penetrating skin, comprising:
   a housing having a blade opening;
   a blade having a sharp edge with a tip that travels along a travel path from a retracted position shielded within the housing to an extended position extending through the blade opening to penetrate the skin;
   a dual-link drive mechanism including a blade link arm coupled to the blade, a rotary drive link arm that is pivotally coupled to and drives the blade arm, and a cam-and-follower guide mechanism that guides movement of the blade arm, wherein the drive arm and the cam-and-follower mechanism cooperatively drive and guide the blade arm to propel the blade tip along the travel path in a rotational and translating motion, wherein the cam-and-follower mechanism includes a non-linear cam surface and a cam follower that is guided by the non-linear cam surface; and
   a trigger operable to actuate the drive mechanism to propel the blade tip along the travel path;
   wherein as the drive arm rotationally drives the blade arm, the blade arm rotates about the cam follower as the cam follower is translationally guided along the non-linear cam surface in a non-linear path to convert the rotary motion of the rotary drive arm to the rotational and translating motion of the blade tip.

2. The fluid-sampling device of claim 1, wherein the non-linear cam surface is defined by a channel formed in the housing and the cam follower is provided by a pin extending from the blade arm and slidingly received in the channel.

3. The fluid-sampling device of claim 1, wherein the cam follower is intermediately positioned on the blade arm between the blade and the pivotal coupling to the drive arm.

4. The fluid-sampling device of claim 1, wherein the non-linear cam surface is generally vertical and curved so that the blade travel path is non-linear and non-symmetrical.

5. The fluid-sampling device of claim 4, wherein the non-linear cam surface is curved so that the blade travel path is generally triangular.

6. The fluid-sampling device of claim 5, wherein the non-linear cam surface is curved so that the generally triangular blade travel path has a descent segment and an ascent segment that is steeper than the descent segment.

7. The fluid-sampling device of claim 1, wherein the drive mechanism further comprises a drive spring that biases the rotary drive arm in a rotary drive direction.

8. The fluid-sampling device of claim 1, wherein the drive mechanism defines a catch surface and the trigger defines a catch surface that engages the drive mechanism catch surface to retain the drive arm in a ready position.

9. A fluid-sampling device for penetrating skin, comprising:
   a housing having a blade opening;
   a blade having a sharp edge with a tip that travels along a travel path from a first retracted position shielded within the housing, through an extended position extending through the blade opening to penetrate the skin, and to a second retracted position shielded within the housing;
   a dual-link drive mechanism including a blade link arm coupled to the blade, a rotary drive link arm that is pivotally coupled to and drives the blade arm, and a cam-and-follower guide mechanism that guides movement of the blade arm, wherein the drive arm and the cam-and-follower mechanism cooperatively drive and guide the blade arm to propel the blade tip along the travel path in a rotational and translating motion, wherein the cam-and-follower mechanism includes a non-linear cam surface and a cam follower that is guided by the non-linear cam surface along a non-linear path so that rotary motion of the rotary drive arm is converted to the rotational and translating motion of the blade tip as the cam follower is translationally guided along the non-linear cam surface, wherein the non-linear cam surface is generally vertical, curved, and arranged so that the travel path of the blade is generally triangular and has a descent segment and an ascent segment that is steeper than the descent segment; and a trigger operable to actuate the drive mechanism to propel the blade tip along the travel path.

10. The fluid-sampling device of claim 9, wherein as the drive arm rotationally drives the blade arm, the blade arm rotates about the cam follower as the cam follower is translationally guided along the non-linear cam surface to convert the rotary motion of the drive arm to the rotational and translating motion of the blade tip.

11. The fluid-sampling device of claim 9, wherein the non-linear cam surface is defined by a channel formed in the housing and the cam follower is provided by a pin extending from the blade arm and slidingly received in the channel, wherein the pin is intermediately positioned on the blade arm between the blade and the pivotal coupling to the rotary drive arm.

12. The fluid-sampling device of claim 9, wherein the drive mechanism further comprises a drive spring that biases the rotary drive arm in a rotary drive direction, and wherein the drive mechanism defines a catch surface and the trigger defines a catch surface that engages the drive mechanism catch surface to retain the rotary arm in a ready position.

13. A blood-sampling device for penetrating skin, comprising:

a housing having a blade opening;

a blade having a sharp tip that travels along a travel path from a first retracted position shielded within the housing, to an extended position extending through the blade opening to penetrate the skin, and to a second retracted position shielded within the housing;

a dual-link drive mechanism including a blade link arm coupled to the blade, a rotary drive link arm that is pivotally coupled to and drives the blade arm, a cam-and-follower guide mechanism that guides movement of the blade arm, and a drive spring that biases the rotary drive arm in a drive direction, wherein the drive arm and the cam-and-follower mechanism cooperatively drive and guide the blade arm to propel the blade tip along the travel path in a rotational and translating motion, wherein the cam-and-follower mechanism includes a non-linear cam surface and a cam follower that is guided by the non-linear cam surface along a non-linear path so that rotary motion of the rotary drive arm is converted to the rotational and translating motion of the blade tip as the cam follower is translationally guided along the non-linear cam surface, wherein as the drive arm rotationally drives the blade arm, the blade arm rotates about the cam follower as the cam follower is translationally guided along the non-linear cam surface to convert the rotary motion of the rotary drive arm to the rotational and translating motion of the blade tip; and a trigger operable to actuate the drive mechanism to propel the blade tip along the travel path.

14. The fluid-sampling device of claim 13, wherein the non-linear cam surface is defined by a channel formed in the housing and the cam follower is provided by a pin extending from the blade arm and slidingly received in the channel, wherein the pin is intermediately positioned on the blade arm between the blade and the pivotal coupling to the drive arm.

15. The fluid-sampling device of claim 13, wherein the non-linear cam surface is generally vertical, arcuate, and arranged so that the blade travel path is generally triangular and has a descent segment and an ascent segment that is steeper than the descent segment.

16. The fluid-sampling device of claim 13, further comprising a removable sterility cap with a shroud portion that fits over the blade tip.

17. The fluid-sampling device of claim 16, wherein the trigger includes a blocked surface and the sterility cap includes a blocking member that contacts the blocked surface to prevent the trigger from being actuated.

18. The fluid-sampling device of claim 13, wherein the drive spring is a torsion spring that biases against the housing and the rotary drive arm.

* * * * *